United States Patent
Galiano (10) Patent No.: US 9,494,507 B2
(45) Date of Patent: Nov. 15, 2016

(54) APPARATUS AND METHOD TO DETERMINE THE BLOOD SEDIMENTATION RATE AND OTHER PARAMETERS CONNECTED THERETO

(71) Applicant: ALIFAX HOLDING SPA, Polverara (IT)

(72) Inventor: Paolo Galiano, Padua (IT)

(73) Assignee: ALIFAX HOLDING SPA, Polverara (IT)

( * ) Notice: Subject to any disclaimer, the term of this patent is extended or adjusted under 35 U.S.C. 154(b) by 0 days.

(21) Appl. No.: 14/418,870

(22) PCT Filed: Jul. 19, 2013

(86) PCT No.: PCT/IB2013/001565
§ 371 (c)(1),
(2) Date: Jan. 30, 2015

(87) PCT Pub. No.: WO2014/020392
PCT Pub. Date: Feb. 6, 2014

(65) Prior Publication Data
US 2015/0300937 A1 Oct. 22, 2015

(30) Foreign Application Priority Data
Jul. 31, 2012 (IT) .............................. UD2012A0137

(51) Int. Cl.
*G01N 15/06* (2006.01)
*G01N 33/00* (2006.01)
(Continued)

(52) U.S. Cl.
CPC .................................... *G01N 15/05* (2013.01)

(58) Field of Classification Search
CPC ....... G01N 15/06; G01N 33/00; G01N 33/48
USPC .......... 422/50, 68.1, 44, 400, 63, 73, 81, 82, 422/82.05, 502, 503, 507, 509; 436/43, 52, 436/53, 63, 66, 68, 69, 70, 71, 164, 171, 436/172, 174, 177, 180
See application file for complete search history.

(56) References Cited

U.S. PATENT DOCUMENTS 5,827,746 A 10/1998 Duic
6,336,358 B1 * 1/2002 Kishimori et al. .......... 73/61.65
(Continued)

FOREIGN PATENT DOCUMENTS

CN 201 173 893 Y 12/2008
DE 202 01 895 U1 7/2002
(Continued)

OTHER PUBLICATIONS

Search Report for PCT/IB2013/001565, dated Jan. 24, 2014.
(Continued)

*Primary Examiner* — Brian J Sines
(74) *Attorney, Agent, or Firm* — Marshall, Gerstein & Borun LLP (57) ABSTRACT

An apparatus to determine the blood sedimentation rate and other parameters connected thereto, carried out by emitting, by means of emitter means, a beam of radiations which passes through a sample being examined, and by detecting, by means of receiver means, the beam of radiations after they have passed through said sample, comprising a reading chamber associated to at least a tube connected to a feed of the sample to be analyzed. Said reading chamber is at least partly transparent to radiations in a certain range of wavelengths, and has at least a substantially rectilinear segment of reduced size into which the sample to be analyzed is introduced. The reading chamber consists of a tube made of plastic material, or glass, defining a capillary channel coupled to said tube in fluidic continuity.

14 Claims, 5 Drawing Sheets

(51) Int. Cl.
*G01N 33/48* (2006.01)
*G01N 15/05* (2006.01)

(56) References Cited

U.S. PATENT DOCUMENTS

| | | | |
|---|---|---|---|
| 6,387,327 B1* | 5/2002 | Ricci et al. | 422/72 |
| 6,632,679 B1* | 10/2003 | Breda | 436/70 |
| 7,005,107 B2 | 2/2006 | Breda | |
| 7,541,191 B2* | 6/2009 | Duic | 436/70 |
| 7,872,734 B2* | 1/2011 | Braig et al. | 356/39 |
| 7,907,985 B2* | 3/2011 | Gable et al. | 600/310 |
| 8,425,843 B2* | 4/2013 | Ciotti et al. | 422/73 |
| 8,900,514 B2* | 12/2014 | Forsell | 422/73 |
| 8,928,877 B2* | 1/2015 | Lim et al. | 356/246 |
| 8,936,755 B2* | 1/2015 | Gable et al. | 422/105 |
| 9,091,676 B2* | 7/2015 | Rule et al. | |
| 2004/0059208 A1 | 3/2004 | Enzo | |
| 2004/0065143 A1 | 4/2004 | Husher | |
| 2009/0311736 A1 | 12/2009 | Ciotti et al. | |

FOREIGN PATENT DOCUMENTS

| | | |
|---|---|---|
| JP | S55 94736 | 7/1980 |
| WO | WO-2004/032702 A2 | 4/2004 |
| WO | WO-2005/022125 A1 | 3/2005 |
| WO | WO-2007/006791 A1 | 1/2007 |
| WO | WO-2007/128684 A1 | 11/2007 |

OTHER PUBLICATIONS

Written Opinion for PCT/IB2013/001565, dated Jan. 24, 2014.

* cited by examiner fig. 1a

STATE OF THE ART fig. 1b

STATE OF THE ART fig. 2 fig. 3 fig. 6 fig. 7

APPARATUS AND METHOD TO DETERMINE THE BLOOD SEDIMENTATION RATE AND OTHER PARAMETERS CONNECTED THERETO

FIELD OF THE INVENTION

The present invention concerns an apparatus and the corresponding method used in the field of medical analyses, to determine the blood sedimentation rate ("ESR"), as well as other parameters connected thereto, either manually or automatically.

BACKGROUND OF THE INVENTION

In the field of medical analyses, pathological conditions, defined as inflammatory, are ascertained by measuring the sedimentation rate of the corpuscular part of the blood, in particular of the erythrocytes, or red corpuscles. In particular, the erythrosedimentation rate represents a non-specific diagnostic test of inflammatory conditions.

The classical or reference method for measuring the sedimentation rate of the blood is the Westergren method.

In recent years, this test has been considerably improved, in particular in terms of execution time, as described, for example, in the patents in the name of Duic U.S. Pat. No. 5,827,746, Breda U.S. Pat. Nos. 6,632,679 and 7,005,107. These patents describe the application of a technique called "stop and flow", which provides to stop the flow of blood under examination inside a capillary tube and to optically measure by means of photometry the speed of aggregation of the corpuscular part of the blood which thickens after it has been stopped.

This technique has allowed on the one hand to reduce the amount of blood needed from a few ml required by the Westergren method to a few hundred micron required by the Breda method, and on the other hand to obtain the results of the measurement in only 20 seconds compared to the sedimentation in the Westergren method, which requires at least one hour's wait.

From document WO2004032702 in the name of Huscher, it is also known to use, instead of an optical/photometric detection, a detection with sound waves which are transmitted toward the tube where the sample to be examined is in transit, and are detected from the opposite side.

It is also known in the state of the art, in particular from WO2005022125, to integrate an apparatus to measure the sedimentation rate with a globule counter device, using the innovative technique of photometric measuring of the sedimentation rate in a capillary, the reduced performance times connected therewith and the low quantities of blood used.

A further improvement was given by WO2007006791, in which the use of particular substances called lactics was proposed, in order to obtain an optimal calibration and setting of the measuring instrument of the erythrosedimentation rate of blood.

Another evolution was shown in WO2007128684 which proposed the use of results obtained with the measuring of the erythro sedimentation rate in order to obtain information regarding a possible anemic condition of the patient.

In all the methods indicated above, which also use different measuring systems, the blood taken from the patients, even in very limited amounts, is introduced into tubular containers and subsequently the necessary measurements are carried out on the blood samples in transit.

One of the problems complained of in this type of optical/photometric measuring but also with other types of radiations, for example sound waves, is that the small Teflon tube normally used has a thickness which can generate an effect of deviating the incident ray with respect to the receiving device.

Moreover, a normal Teflon tube can have, in its manufacturing by extrusion, differences in thickness and section precisely in correspondence to the point where it is hit by the incident ray. Such differences in thickness and section of the Teflon tube, if they are at the point where the emitter creates deflections of the ray passing through, generate a disturbance and a non-linear reading which makes it difficult to calibrate the detection system so as to obtain repeatable instruments in the production stage.

Since the surfaces of the tube are not perpendicular to the incident radiations and have a refraction index that is different from the mean (air) in which the incident radiation is emitted and received, the surfaces of the capillary act as a lens, altering the geometry of the front of the incident wave.

Figure 1A:
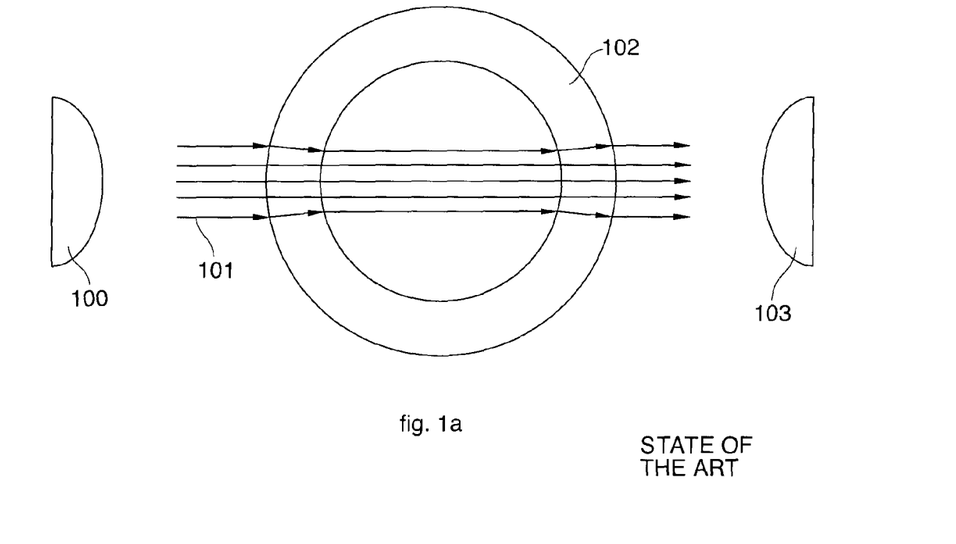
FIGS. 1a and 1b schematically show the problems connected to the use of capillary tubes made of Teflon in the state of the art.
Figure 1B:
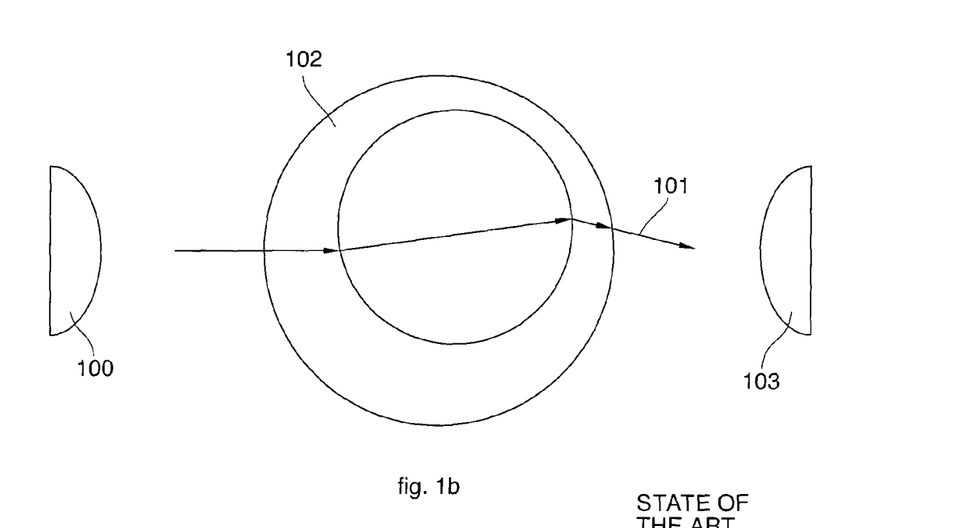

The attached drawings 1a and 1b graphically show the situation of the state of the art, in which an emitter 100 emits a radiation 101 toward a Teflon tube 102 and on the opposite side there is a receiver 103 which detects the radiation after it has passed through the sample to be examined (not shown) present inside the Teflon tube 102.

As can be seen in FIG. 1a, the waves 101 are deflected four times as they pass through the thickness of the Teflon tube 102, so that it does not guarantee the precision of the result of the measurement.

In FIG. 1b it can be seen how even a collimated central ray can be deflected as it passes through the Teflon tube 102, in particular when its section is particularly non-uniform on the circumference, as shown in an accentuated form in the drawing, because of the tolerances of coaxiality between internal and external diameter of the tube.

It has been found that it is practically impossible to produce industrially Teflon tubes guaranteed with a constant section for the whole of their length, because the process of manufacturing by extrusion is a known technical limit.

As we said, however much an incident radiation is collimated to strike the tube in its central part, often these variations in thickness, caused by the impossibility of obtaining a standardized precision during production, induce errors in the optical measuring, so that an instrument can give different readings from instrument to instrument.

This problem is partly resolved using tubes with a greater diameter than is necessary (and as a consequence samples with a greater volume) or by using diffusive materials/surfaces (for example Teflon with respect to electromagnetic radiations) which however, reduce the sensitivity of the instrument.

Another considerable problem complained of in the use of this measuring technology concerns the contamination of the reading chamber between successive measurements. Indeed, after every measurement, and after the analysis, the blood sample is discharged and a new blood sample is introduced into the measuring volume.

Given that the ESR measurement is a physical measurement of the characteristics of sedimentation by the red corpuscles, for this type of test it is important to be certain that in a continuous stream of samples, there is no contamination between one sample and the next at the measuring point of the test.

To avoid having to wash the measuring volume after the discharge, the residues of the sample already analyzed are discharged by the new blood sample to be analyzed, as the hydraulic path which the blood has to follow in order to avoid pollution is rather long, which increases the volume of blood to be used, as well as the performance times.

In relation to the problems identified above, one purpose of the present invention is to supply a method, and the corresponding apparatus, to determine the sedimentation rate of blood, as well as other parameters correlated thereto, which allow an extremely quick analysis, easy and very reliable and precise.

Another purpose is to avoid washing between sequential samples, so as to achieve a simplification in the flow of work applied to an automatic, semi-automatic or manual instrument.

Another purpose of the invention is to produce a compact and easily transportable apparatus, practical to use in any condition or environment, and also usable as a disposable instrument in a surgery or hospital, in the so-called POC (Points of Care) for example.

The Applicant has devised and embodied the present invention to obtain these purposes and also other advantages.

SUMMARY OF THE INVENTION

The present invention is set forth and characterized in the independent claims, while the dependent claims describe other characteristics of the invention or variants to the main inventive idea.

The apparatus to determine ESR according to the present invention comprises, in its general structure, a reading chamber equipped with a through transit channel with a controlled section; the reading chamber is made of a material that is transparent to radiations in a certain range of wavelengths, and has at least a substantially rectilinear segment with an extremely reduced size within which the blood to be analyzed is introduced and made to transit.

The transit channel is defined between an entrance hole and an exit hole, which are connected to respective feed and discharge ends of a tube, made of Teflon for example, which serves to transport the blood sample toward the reading chamber and to discharge the sample from the reading chamber after the measurement has been made.

By radiations, here and hereafter in the description, we refer both to electromagnetic waves, in particular to those in the visible field, and to different waves which follow the principles of wave mechanics, such as for example, but not only, sound waves, or any other type of radiation usable in the context.

Therefore, even if hereafter, in particular in the detailed description of the drawings, we shall refer to luminous radiations and emitters/receivers of the optical type, it is understood that the invention is equally applicable to all types of radiation as indicated above.

The apparatus also comprises pump means able to send a blood sample inside the reading chamber, so that the blood sample can be passed through by a radiation emitted by emitter means and detected by mating receiver means disposed in correspondence to a point of the reading chamber, on the opposite side with respect to the emitter means.

The receiver means are connected to a processing unit able to transform the values detected into an expression of the sedimentation rate, or other parameters connected thereto, in a unit of measurement compatible with the units normally used.

In a manner known in the state of the art, the pump means are suitable to abruptly interrupt the flow of blood flowing through the reading chamber, so as to cause a stopped-flow and therefore an aggregation and sedimentation of the blood corpuscles thanks to its compaction.

This compaction causes a variation in the signal detected by the detection means with a consequent acquisition of information useful to determine the ESR.

According to a first feature of the present invention, the reading chamber consists of a body with a through channel of a capillary size; the body has for example a cylindrical section, even if this shape is not restrictive in itself, and is made of plastic material, for example, but not only, acrylic, or glass. The transit channel, made passing through the body which defines the reading chamber, has respective entrance and exit holes associated to respective ends of a feed tube and, respectively, a discharge tube of the blood to be analyzed.

The use of such materials, such as acrylic or glass, allows the body, for example cylindrical, which defines the reading chamber to be modeled, and in particular, in the entrance surfaces of the radiation detected by the receiver means.

In particular, the particular shape of the reading chamber made of acrylic or glass is made so that the entrance zone of the light, the sound waves, or other suitable radiation, has a substantially flat surface, and suitably shaped, instead of a curvilinear surface as occurs in the case of the traditional Teflon tube.

According to another evolutionary characteristic, the reading/measuring chamber has a flat surface at its opposite end as well, that is, the exit end, so that the path of the optical, sound or other radiation is not deflected/refracted by curves which alter the information content.

In particular, these reading windows with their flat surface interact with the radiation incident thereto in an independent manner from their position inside the standard positioning tolerances for mechanical workings.

According to another variant of the invention, these flat windows constitute transparent surfaces, not diffusive like those of a normal Teflon tube, and allow to obtain a much bigger optical or sound detection sensitivity.

According to a variant of the invention, the reading chamber with its holed body made of acrylic material or glass is connected to a tube of the conventional type, made of Teflon for example, upstream and downstream, in which the movement of the blood sample occurs.

In another characteristic, the reading chamber in glass or acrylic is housed inside a rigid container which defines the housing seatings for the tubes upstream and downstream which define the path of the blood sample to be analyzed.

In another form of embodiment, the rigid container also has collimation means which define the path of the optical, sound or other type of beam, which passes through the reading chamber.

According to another characteristic of the present invention, thanks to the characteristics of the apparatus and in particular of the measuring cell as described above, the measuring method allows to avoid the contamination between one sample and another, thus avoiding the so-called "carryover" phenomenon which causes contamination between successive samples which entails distorted measurements or the need for washing between samples.

The method according to the present invention provides that extremely limited amounts of blood sample are taken, able to promote pediatric blood samples or via capillaries, in the order of 20-30 micro-liters for example.

According to the invention, the device comprising emitters and receivers is situated at a determined point of the blood flow which corresponds to the end of travel of each sample read.

By using the reading chamber made of acrylic or vitreous material, situated inside the rigid support, and thanks also to the collimation of the radiation emitted, it is possible, according to the invention, to always measure the end part of the sample, the so-called tail of the sample, which has no contamination from the previous sample.

Moreover, in this way, all the blood samples which follow are not contaminated by the previous sample at the measuring point.

In one form of embodiment of the invention, the volume of blood in the reading chamber is 1 microliter, while the amount of blood in each pediatric sample per single patient can even be 20 or 30 micro-liters.

According to one characteristic of the invention, the reading and measuring point is situated in a position, with respect to the measuring chamber and in particular to the tube in glass or acrylic, so that 25 microliters of blood pass and are made to flow through the reading chamber as an inert passage without any measuring of this part.

The reading of the sample is started for a portion of 1 microliter of volume on the last 5 microliters of initial volume.

The passage of 20 microliters of inert blood through the reading chamber of 1 microliter has the function of a mechanical or washing thrust equal to the ratio of 20 times with respect to the volume of 1 microliter.

The thrust volume of 20 microliters on which no measurement is carried out allows to offer in the last 5 microliters no contamination between samples, therefore the passage of the sample to be analyzed has a self-washing effect with respect to the previous sample.

Thanks to this, the invention allows to carry out drop measurements from a capillary sample (25 microliters) and at the same time does not require any washing between samples, making it particularly suitable for use in the so-called Points Of Care (POC) and in pediatric use.

In short, the advantages offered by the present invention, and in particular the conformation and the structure of the reading chamber, are the following:
- it is possible to carry out ESR measurings with a reduced volume of the sample, which is particularly indicated for pediatric patients and capillary samples;
- there are no reductions in precision of the measurement due to the deflection of the radiations deriving from the problems connected to the manufacturing of Teflon tubes;
- both the pediatric samples and the samples taken from adult patients use the auto-washing system of the sample, preventing carryover between one sample and the next;
- experimental ESR measuring trials of alternately high and low samples corroborate the same results even inverting the same samples.

In the apparatus according to the invention, the reading chamber, the blood sampling means and the optical detection system can constitute a transportable structure which is distinct and separate from the processing unit and from a possible display system of the results, and can be connected to them using transmission cables or also by radio.

In this way, extreme flexibility and versatility of use is obtained, because the sample taking and analysis instrument can have reduced sizes which allow it to be used, for example, even directly from the bed of the patient, or in any case in difficult conditions.

It is also possible to both use a plurality of such apparatuses in parallel, for the simultaneous performance of the same analysis on different blood samples, and also to use the same apparatus in series with other devices able to perform different types of hematologic analyses on the same sample.

Moreover, also because of the very limited time needed for the analysis, the apparatus can also be used in local surgeries, in local outpatient centers, in mobile blood units, or, as we said, integrated on apparatuses intended for hematologic analyses of another type.

The continuous study of the flow can also be used to determine other parameters of the rheology of the blood, such as density or viscosity.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 2:
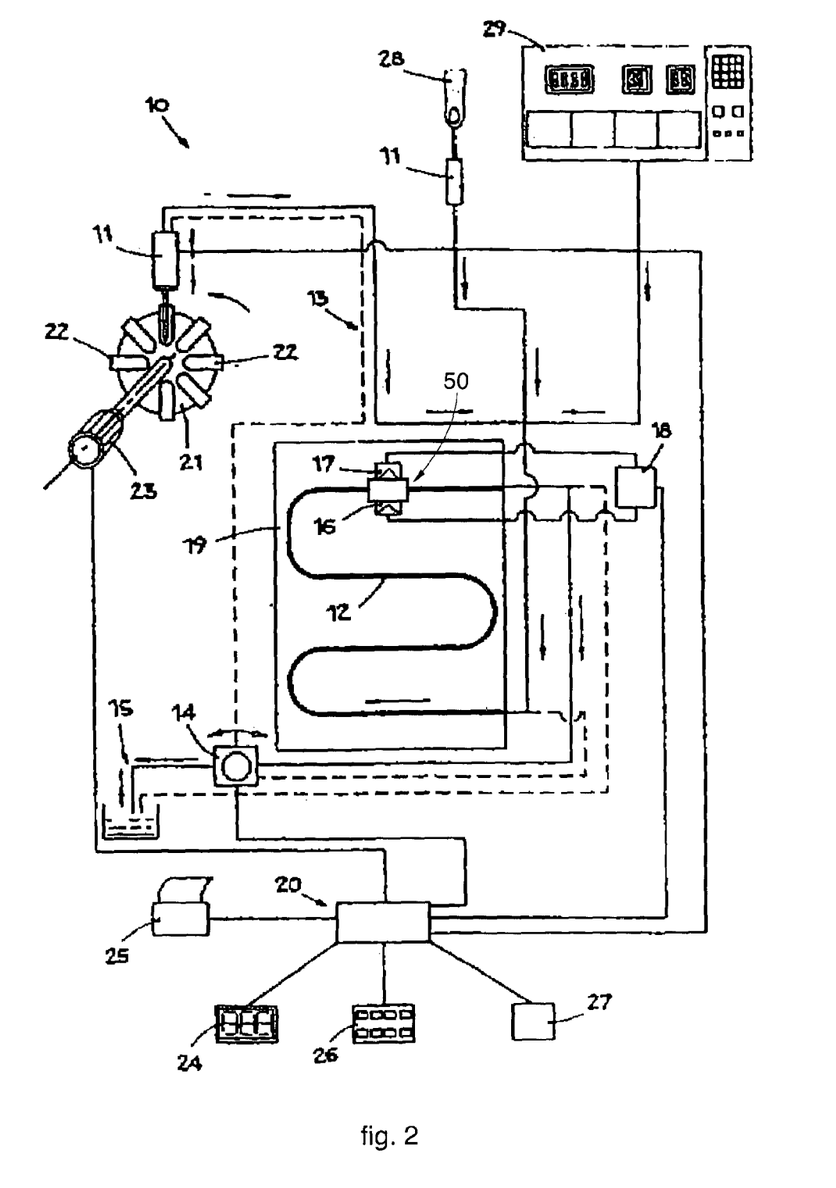
FIG. 2 schematically shows the apparatus to determine the sedimentation rate of blood and other parameters according to the invention.

FIG. 2 schematically but not restrictively shows an apparatus 10 to determine the sedimentation rate of blood and of other parameters connected thereto, which mainly comprises the following components:
- a member 11 for sampling the blood to be analyzed;
- a tube 12, made of Teflon for example, inside which the blood sample is able to be introduced, which transports the sample toward a reading chamber 50, which comprises, in this non-restrictive case (FIGS. 4 and 5), a body consisting of a small cylinder 51 (hereafter defined cylindrical body 51) made of plastic material, for example acrylic, or glass, transparent to electromagnetic radiations in a field comprised between 100 and 2000 nm, preferentially between 200 and 1000 nm;
- a circuit 13 which connects the sampling member 11 to the tube 12 and inside which the blood sample circulates;
- an instantaneous locking pump 14 associated to the circuit 13;
- a discharge pipe 15 to discharge the blood sample after analysis;
- a measuring instrument comprising a radiation emitter device 16 associated to a mating detector device 17, in this case disposed on opposite sides with respect to the cylindrical body 51 defining the reading chamber 50;
- a control and processing unit 20 able to manage the functioning of the apparatus 10 and an interface unit 18 by means of which the devices 16 and 17 are connected to the control and processing unit 20.

The sampling member 11, in this case a syringe, is able to selectively take the sample of blood to be analyzed from the containers 22 of a storage drum 21, which can be made to rotate by a small motor 23.

In the form of embodiment shown, the sampling member 11 can also be used to take a sample of native blood directly from the finger 28 of a patient, for example carried out with a lancet device of the finger pricking type and containing the capillary 51 and the devices 16, 17 inside it.

Moreover, the blood can also reach the tube 12 from an apparatus 29 suitable to carry out other analyses, inside which the whole apparatus 10 can be integrated; in this way blood which has already been homogenized and does not require any other additional treatments arrives at the reading chamber 50.

In a variant, the sampling member 11 is integrally provided with agitator means to homogenize the blood sample taken.

The tube 12, in the non-restrictive solution shown, is associated to a metal support 19 provided with thermostatting means which allow it to be maintained at a constant temperature which can be preset as desired, conditioning the temperature at which the analysis is carried out.

The pump 14, can be disposed either upstream or downstream of the tube 12, is able to drive the sampling member 11 to make the blood sample circulate inside the circuit 13 and the tube 12, and also has the function of interrupting the flow of the sample instantaneously.

In a preferential form, the pump 14 is reversible and is able to allow the blood to circulate inside the circuit 13 in the two directions indicated respectively in a continuous line (aspiration) and a broken line (thrust).

The interface unit 18 is able to activate/de-activate the emitter device 16 and to translate the signals picked up by the receiver device 17 into readable signals to the control and processing unit 20.

The control and processing unit 20, consisting of an electronic processor of the microprocessor type, is programmable to manage different functioning modes of the apparatus 10.

It comprises a data base or internal memory 27 in which a series of parameters are contained, in the form of numerical data, tables or graphs.

The control and processing unit 20 also comprises user interface means, in this case consisting of a keyboard 26 for the insertion of data, a monitor or display 24 and a printer 25 to display the results of the analysis and to process them for statistical purposes.

The reading chamber 50 is made in a rigid container 52 (FIG. 4) which in this case has a central through hole 54 where the cylindrical body 51 is housed. According to a variant, the cylindrical body 51 is housed in a closed volume defined by transparent lenses (not visible in the drawings) disposed to close the through hole 54.

Figure 3:
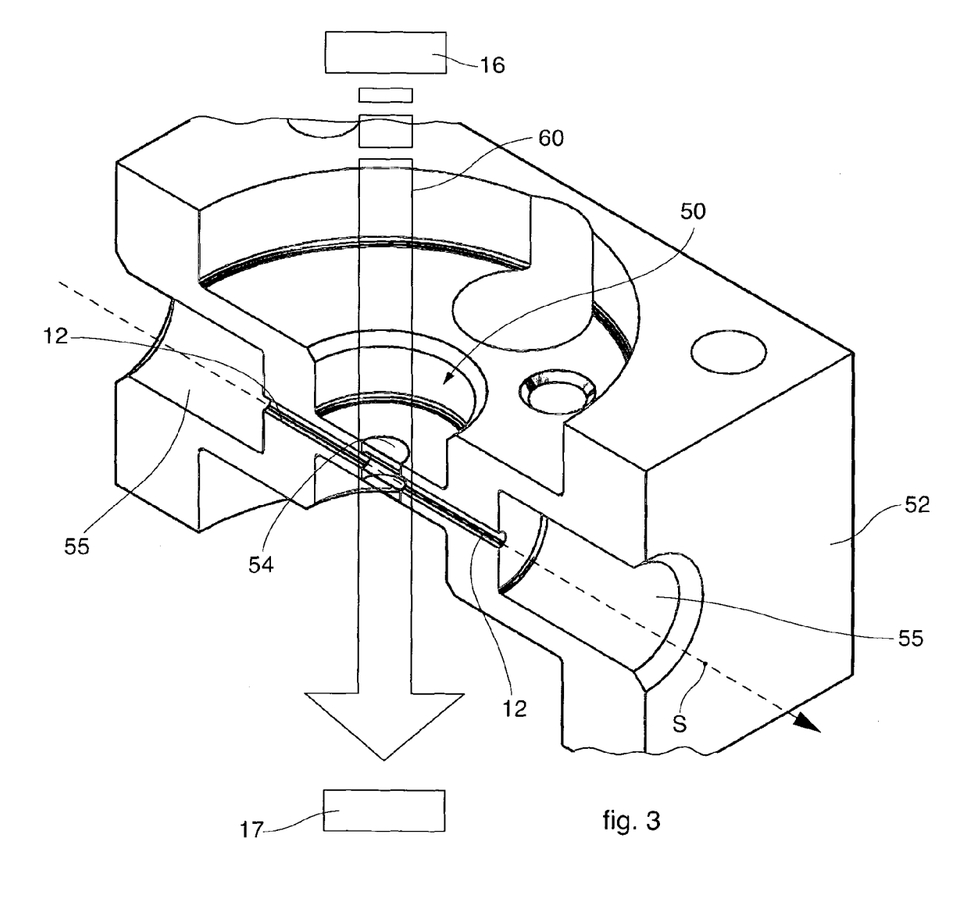
FIG. 3 shows a cut-away view of the container and the reading chamber according to the present invention with the optical emission and reception system schematized.

By means of a pair of holes, respectively front 56a and rear 56b, the cylindrical body 51 connects upstream and downstream to the respective feed and discharge ends of the tube 12. In this way, the blood sample under examination can flow in a forced manner, in the direction S indicated in FIG. 3, through the transit channel 58 defined inside the cylindrical body 51 between the two holes 56a, 56b, respectively entrance and exit, so that the beam of electromagnetic waves emitted by the emitter device 16 passes through it. As can be seen in FIG. 3, the beam of electromagnetic waves passes through the cylindrical body 51 in a direction substantially orthogonal to the direction of movement of the blood sample defined by the transit channel 58.

Figure 4:
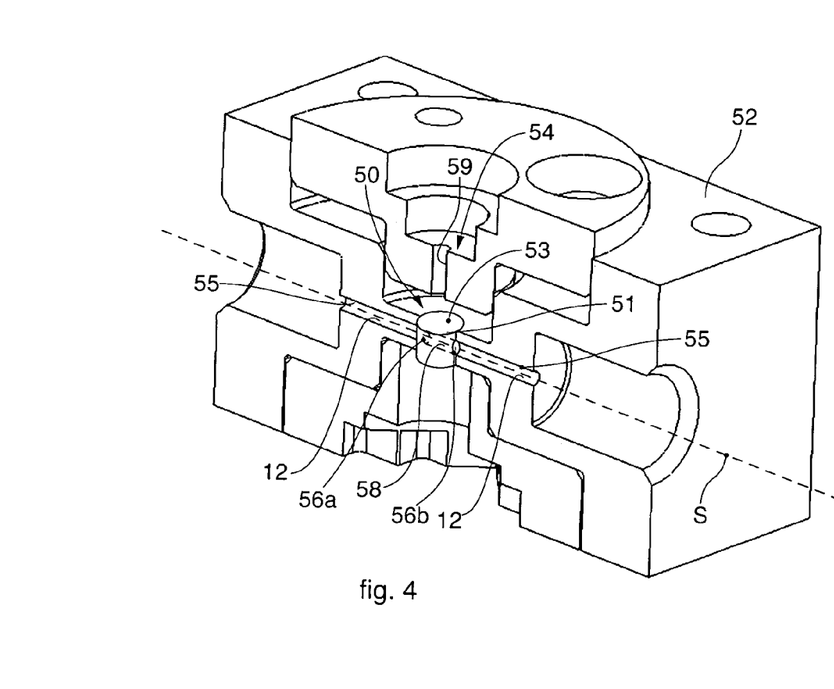
FIG. 4 shows the detail of the reading chamber in greater detail.
Figure 5:
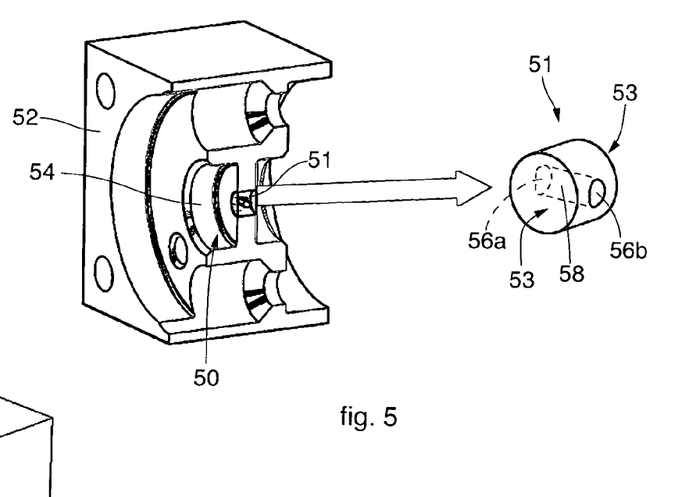
FIG. 5 shows an exploded view with the reading chamber disassociated from the rigid container.

The rigid container 52 has housing seatings 55 for the corresponding segments of the tube 12, in order to guarantee an optimal and stable fluidic connection between tube 12 and cylindrical body 51.

The emitter device 16 and the mating detector device 17 are facing and opposite the cylindrical body 51 and are able respectively to emit and detect electromagnetic radiations whose wavelength is advantageously comprised between 200 and 1000 nm.

The cylindrical body 51 has flat surfaces 53 opposite and facing toward the emitter device 16 so that the path of the electromagnetic wave, indicated with the number 60, is not deflected/refracted by curves which alter the information content thereof.

The rigid container 52 has channelings 59 (FIG. 4) which allow the beam of electromagnetic waves to be concentrated only in correspondence to the cylindrical body 51, so that only a portion of the blood sample is involved in the measuring. In particular, as will be seen better hereafter, the reduced portion of the sample subjected to analysis allows to obtain the important self-washing effect between one sample and the next.

Thanks to the use of the cylindrical body 51, the incidence of geometric tolerances and manufacturing tolerances on the precision of the measurement is reduced if not eliminated, since the optical signal is perfectly collimated and is not deflected or altered by thicknesses or disturbing elements. It must also be considered that glass or acrylic material, intrinsically, do not suffer from the problems connected to the use of traditional Teflon tubes.

Moreover, the use of the cylindrical body 51 as described above allows to suitably design the entrance surface of the radiation emitted by the emitter device 16.

For example, in relation to the emission characteristics (type of wave, wavelength, distance, etc.) it is possible to size the entrance surface of the radiation in order to obtain inside the device a flat wave with a constant intensity around the channel where the sample passes. In this way it is possible to obtain a high level of insensitivity to the positioning errors of said channel, so that the measurement will guarantee high repeatability irrespective of possible inaccuracies of assembly, and also guarantees an increase in the sensitivity so that the measurement can be carried out even with quantities in the order of a microliter of sample to be analyzed.

The present invention, in an evolutionary variant not shown in the drawings, can provide to interpose a collimator lens between the emitter device 16 and the cylindrical body 51, with the purpose of further improving the precision of incidence of the electromagnetic waves.

In a variant, this collimation effect can be obtained by means of suitable working of the glass or acrylic surface of the cylindrical body 51.

Figure 6:
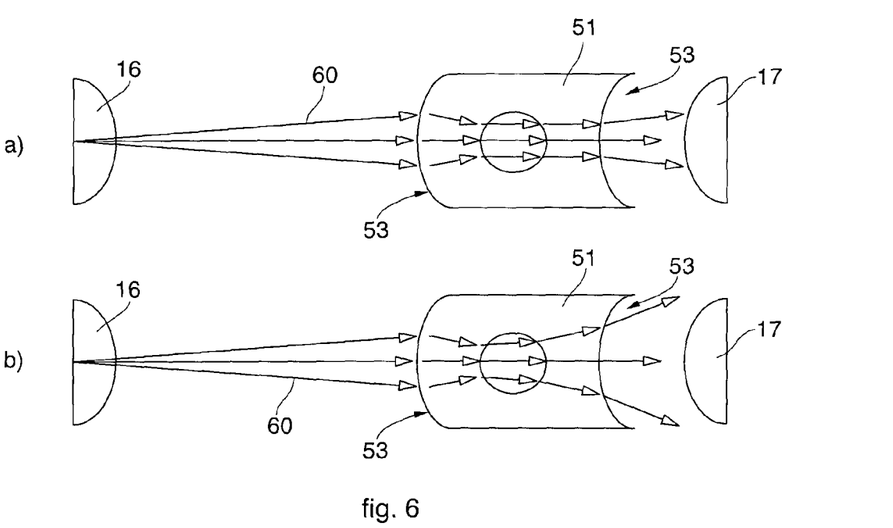
FIG. 6 shows a schematization of the functioning of the apparatus according to the present invention.

With reference to FIG. 6 it can be seen how the sample of liquid (blood or other) transiting inside the cylindrical body 51 comes to constitute a sort of lens whose behavior is linked to the refraction index of the liquid itself, which is different from the refraction index of glass or acrylic material. In FIG. 6 it can be seen how the waves are deflected differently in the passage through the sample in case a) compared with case b).

Thanks to the present invention it is therefore possible to carry out other types of measurements, such as for example measurements of the refraction index of the plasma which supplies indications on the content of proteins in the blood.

This allows the apparatus 10 according to the present invention to carry out the following functions:

- to measure absorption, rendering the measurement of the optical density (imaginary part of the refraction index) independent from the protein content (real part of the refraction index);
- to measure the refraction index of the plasma from whole blood and from plasma;
- to measure a synergy of the two sizes (measuring both the real part and the imaginary part of the refraction index) in order to be able to obtain the measurement of the ZSR (Zeta Sedimentation Rate) which is an alternative test to the measurement of the ESR in which the test tube containing the sample is turned upside down before being subject to measuring;
- to measure the refraction index in the real and imaginary part of the blood comparing the values thereof during the flow of the blood in the polarizations of the parallel electric field perpendicular to the flow.

Figure 7:
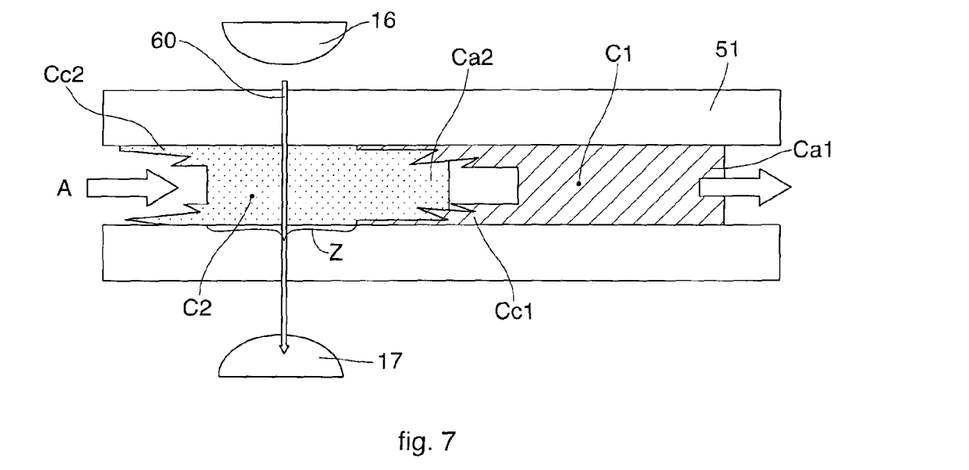
FIG. 7 shows a schematization of the method according to the present invention with the problem of contamination between subsequent samples eliminated.

With reference to FIG. 7, we can see how using the reading chamber 50 with the cylindrical body 51 defining the transit channel 58 for the sample to be analyzed having the characteristics as described above can also promote sequential measuring methods, which reduce the phenomenon of contamination between different samples, known by the term "carryover".

Indicating with A the arrival direction of the flow of the sample, for example blood, it can be seen how the first sample C1 has a head Ca1 and a tail Cc1, which contaminates with its rear ends part of the head Ca2 of the second sample C2.

However, since the reading zone Z can be limited to a rectilinear segment with an extremely reduced length, the sample subjected to reading is only an intermediate fraction, possibly comprising the tail Cc2, which is not affected by the contamination of the previous sample. Indeed, the head Ca2 of the next sample C2 acts as a washing element of the residues of the previous sample, so that the intermediate part and the tail of the next sample are without traces of contamination.

The reduced quantity of sample inside the cylindrical body 51 therefore allows to concentrate the position of the emitter 16/receiver 17 system in a clean zone so as to eliminate the negative effects of the "carryover" phenomenon.

Modifications and/or additions of parts may be made to the apparatus as described heretofore, without departing from the field and scope of the present invention.

For example, the emitter 16 and receiver 17 devices can be positioned on the same side of the cylindrical body 51 and detect the reflection of the radiation emitted.

Moreover, the emitter device 16 can be predisposed for the emission of polarized light in order to obtain characteristic analysis results as a function of the polarization.

Or the instantaneous stoppage of the flow of the blood sample can be carried out by means of valve means associated to the circuit 13 and/or the tube 12.

The invention claimed is:

1. Apparatus to determine the blood sedimentation rate and other parameters connected thereto, carried out by emitting, by means of emitter means, a beam of radiations which passes through a sample being examined, and by detecting, by means of receiver means, the beam of radiations after they have passed through said sample, comprising a reading chamber associated to at least a tube connected to a feed of the sample to be analyzed, said reading chamber being at least partly transparent to radiations in a certain range of wavelengths, and having at least a substantially rectilinear segment of reduced size into which the sample to be analyzed is introduced, wherein the reading chamber consists of a body made of plastic material, or glass, having an entrance hole and an exit hole able to be selectively coupled to respective feed and discharge ends of said tube, a through transit channel of a capillary size being defined between said entrance hole and said exit hole for the passage of the blood sample to be analyzed.

2. Apparatus as in claim 1, wherein said plastic material is acrylic material.

3. Apparatus as in claim 1, wherein said body with a through transit channel has at least a flat surface facing, during use, one or more of the emitter means and/or the receiver means.

4. Apparatus as in claim 3, wherein said at least one flat surface is worked so as to be transparent non-diffusive.

5. Apparatus as in claim 1, wherein said body with through transit channel is housed inside a rigid container.

6. Apparatus as in claim 5, wherein said rigid container defines housing seatings for segments of the tube upstream and downstream of the body with through transit channel.

7. Apparatus as in claim 5, wherein said rigid container has means defining the path of the radiations which pass through the body with through transit channel.

8. Apparatus as in claim 1, wherein, in correspondence to the position of the body with through transit channel, said rigid container has a positioning through hole.

9. Apparatus as in claim 8, wherein said through hole is closed on at least one side by transparent lenses.

10. Apparatus as in claim 1, wherein it comprises at least a collimator lens disposed between the emitter means and the body with through transit channel.

11. Apparatus as in claim 1, wherein said radiations are chosen among electromagnetic waves, in particular the ones in the visible range, sound waves, or any other type of suitable radiation.

12. Method to determine the blood sedimentation rate and other parameters connected thereto, carried out by emitting, by means of emitter means, a beam of radiations which pass through a sample being examined, and by detecting, by means of receiver means, the beam of radiations after they have passed through said sample, in which a reading chamber is associated to at least a tube connected to a feed of the sample to be analyzed, said reading chamber being at least partly transparent to radiations in a certain range of wavelengths, and having at least a substantially rectilinear segment of reduced size into which the sample to be analyzed is introduced, wherein it provides that a quantity of the sample to be analyzed comprised between 20 and 30 microliters is sent into a reading chamber defined by a body with through transit channel made of plastic material or glass and fluidically connected, by means of a respective entrance hole and exit hole, defining between them said transit channel, to a feed tube; in that the emitter means and the receiver means are disposed facing flat surfaces of said body with through transit channel at a determined point of the blood flow which corresponds to the end-of-travel of each sample read; and in that the measurement is caffied out on an end portion of the sample after a head part thereof has passed, so that said head part performs the function of washing out the contamination of the previous sample.

13. Method as in claim 12, wherein the volume of the sample to be analyzed in the reading chamber of the body with through transit channel is in the order of 1 microliter.

14. Method as in claim 12, wherein it provides to make measurements of the refraction index of the sample in transit in the body with through transit channel thanks to the difference between the refraction index of the sample and the refraction index of the material that makes up the body with through transit channel.

* * * * *